(12) United States Patent
Bär

(10) Patent No.: US 6,303,789 B1
(45) Date of Patent: Oct. 16, 2001

(54) BENZAMIDES WITH TETRAHYDROFURANYLOXY SUBSTITUTENTS AS PHOSPHODIESTERASE 4 INHIBITORS

(75) Inventor: Thomas Bär, Reichenau (DE)

(73) Assignee: Byk Gulden Lomberg Chemische Fabrik GmbH, Constance (DE)

( * ) Notice: Subject to any disclaimer, the term of this patent is extended or adjusted under 35 U.S.C. 154(b) by 0 days.

(21) Appl. No.: 09/701,566

(22) PCT Filed: May 27, 1999

(86) PCT No.: PCT/EP99/03669

§ 371 Date: Dec. 7, 2000

§ 102(e) Date: Dec. 7, 2000

(87) PCT Pub. No.: WO99/64414

PCT Pub. Date: Dec. 16, 1999

(30) Foreign Application Priority Data

Jun. 10, 1998 (EP) .................................................. 98110710

(51) Int. Cl.[7] ...................... C07D 405/12; C07D 307/20; C07D 309/10; A61K 31/341; A61K 31/443

(52) U.S. Cl. .................................... 546/284.4; 546/282.1; 546/283.1; 549/417; 549/476; 549/478; 514/336; 514/460; 514/473

(58) Field of Search .............................. 546/284.4, 282.1, 546/283.1; 549/417, 476, 478; 514/336, 460, 473

(56) References Cited

FOREIGN PATENT DOCUMENTS

| | | |
|---|---|---|
| 93/25517 | 12/1993 | (WO) . |
| 94/02465 | 2/1994 | (WO) . |
| 95/20578 | 8/1995 | (WO) . |
| 96/03399 | 2/1996 | (WO) . |
| 97/20833 | 6/1997 | (WO) . |
| 98/07715 | 2/1998 | (WO) . |

*Primary Examiner*—Ba K. Trinh
(74) *Attorney, Agent, or Firm*—Jacobson Holman, PLLC

(57) ABSTRACT

Compounds of the formula I

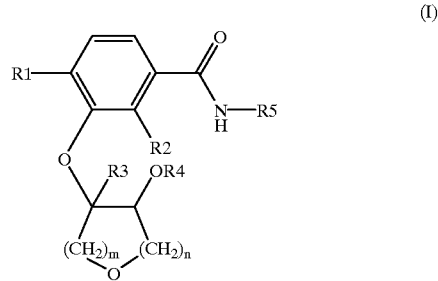

in which R1, R2, R3, R4, R5, m and n have the meanings cited in the description, are novel effective PDE-inhibitors.

10 Claims, No Drawings

BENZAMIDES WITH TETRAHYDROFURANYLOXY SUBSTITUTENTS AS PHOSPHODIESTERASE 4 INHIBITORS

This application is a 371 of PCT/EP 99/03669 dated May 27, 1999.

FIELD OF APPLICATION OF THE INVENTION

The invention relates to novel benzamides which are used in the pharmaceutical industry for the production of medicaments.

1. Known Technical Background

The international patent applications WO93/25517, WO95/01338 and WO96/03399 disclose trisubstituted phenyl derivatives as selective PDE4 inhibitors. The international patent applications WO94/02465 and WO95/20578 also describe 3- or polysubstituted phenyl derivatives as inhibitors of phosphodiesterase 4 and of TNF secretion.

2. Description of the Invention

It has now been found that the compounds described below in greater detail, which differ from the previously published compounds by a different type of substitution, have surprising and particularly advantageous properties.

The invention thus relates to compounds of the formula I,

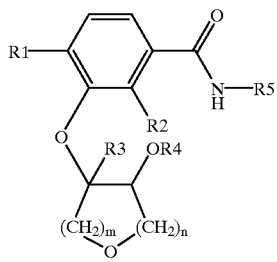

(I)

in which

R1 is 1–6C-alkoxy, 3–7C-cycloalkoxy, 3–7C-cycloalkylmethoxy, benzyloxy or 1–4C-alkoxy which is completely or predominantly substituted by fluorine, R2 is hydrogen and R3 is hydrogen or R2 and R3 are together a methylene group, R4 is hydrogen, 1–8C-alkyl, 1–6C-alkoxy-1–4C-alkyl, 1–6C-alkylthio-1–4-alkyl, 1–6C-alkylsulfonyl-1–4C-alkyl, alkyl, 1–6C-alkylsulfonyl-1–4C-alkyl, 1–8C-alkylcarbonyl, 3–7C-cycloalkyl, 3–7C-cycloalkymethyl, phenyl-1–4C-alkyl or 1–4C-alkyl which is completely or predominantly substituted by fluorine, R5 is phenyl, pyridyl, phenyl substituted by R51, R52 and R53 or pyridyl substituted by R54, R55, R56 and R57, where R51 is hydroxyl, halogen, cyano, carboxyl, trifluoromethyl, 1–4C-alkyl, 1–4C-alkoxy, 1–4C-alkoxycarbonyl, 1–4C-alkylcarbonyl, 1–4C-alkylcarbonyloxy, amino, mono- or di-1–4C-alkylamino or 1–4C-alkylcarbonylamino, R52 is hydrogen, hydroxyl, halogen, amino, trifluoromethyl, 1–4C-alkyl or 1–4C-alkoxy, R53 is hydrogen, halogen, 1–4C-alkyl or 1–4C-alkoxy, R54 hydroxyl, halogen, cyano, carboxyl, 1–4C-alkyl, 1–4C-alkoxy, 1–4C-alkoxycarbonyl or amino, R55 is hydrogen, halogen, amino or 1–4C-alkyl, R56 is hydrogen or halogen and R57 is hydrogen or halogen, n is 1 or 2, m is 1 or 2, where the sum of m and n may only assume the values 2 or 3, the salts of these compounds and the N-oxides of the pyridines and their salts.

1–8C-Alkyl is straight-chain or branched alkyl radicals having 1 to 8 carbon atoms. Examples which may be mentioned are the octyl radical, isooctyl radical (6-methylheptyl radical), heptyl radical, isoheptyl radical (5-methylhexyl radical), hexyl radical, isohexyl radical (4-methylpentyl radical), neohexyl radical (3,3-dimethylbutyl radical), pentyl radical, isopentyl radical (3-methylbutyl radical), neopentyl radical (2,2-dimethylpropyl radical), butyl radical, isobutyl radical, sec-butyl radical, tert-butyl radical, propyl radical, isopropyl radical, ethyl radical and the methyl radical.

1–4C-Alkyl is straight-chain or branched alkyl radicals having 1 to 4 carbon atoms. Examples which may be mentioned are the butyl radical, isobutyl radical, sec-butyl radical, tert-butyl radical, propyl radical, isopropyl radical, ethyl radical and methyl radical.

1–6C-Alkoxy is a radical which, in addition to the oxygen atom, contains a straight-chain or branched alkyl radical having 1 to 6 carbon atoms. Examples of alkoxy radicals having 1 to 6 carbon atoms which may be mentioned are the hexyloxy radical, isohexyloxy radical (4-methylpentyloxy radical), neohexyloxy radical (3,3-dimethylbutoxy radical), pentyloxy radical, isopentyloxy radical (3-methylbutoxy radical), neopentyloxy radical (2,2-dimethylpropoxy radical), butoxy radical, isobutoxy radical, sec-butoxy radical, tert-butoxy radical, propoxy radical, isopropoxy radical, ethoxy radical and the methoxy radical.

3–7C-Cycloalkoxy is cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkylmethoxy is cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

Examples of 1–4C-alkoxy which is completely or predominantly substituted by fluorine which may be mentioned are the 2,2,3,3,3-pentafluoropropoxy radical, the perfluoroethoxy radical, the 1,2,2-trifluoroethoxy radical in particular the 1,1,2,2-tetrafluoroethoxy radical, the 2,2,2-trifluoroethoxy radical, the trifluoromethoxy radical and preferably the difluoromethoxy radical.

1–6C-Alkoxy-1–4C-alkyl is one of the above-defined 1–4C-alkyl radicals which is substituted by a 1–6C-alkoxy radical. Examples which may be mentioned are the methoxymethyl radical, t-butoxymethyl radical, 1-ethoxyethyl radical and the 1-methyl-1-methoxyethyl radical.

1–6C-Alkylthio-1–4C-alkyl is a 1–4C-alkyl radical which is substituted by a 1–6C-alkylthio radical. Examples which may be mentioned are the methylthiomethyl radical and the tert-butylthiomethyl radical.

1–6C-Alkylsulfinyl-1–4C-alkyl is a 1–4C-alkyl radical which is substituted by a 1–6C-alkylsulfinyl radical. An example which may be mentioned is the methylsulfinylmethyl radical.

1–6C-Alkylsulfonyl-1–4C-alkyl is a 1–4C-alkyl radical which is substituted by a 1–6C-alkylsulfonyl radical. An example which may be mentioned is the methylsulfonylmethyl radical 1–8C-Alkylcarbonyl is a radical which, in addition to the carbonyl group, contains one of the abovementioned 1–8C-alkyl radicals. An example which may be mentioned is the acetyl radical, propanoyl radical and the butanoyl radical.

3–7C-Cycloalkyl is cyclopropyl, cyclobutyl, cyclopentyl, cyclohexyl and cycloheptyl, of which cyclopropyl, cyclobutyl and cyclopentyl are preferred.

3–7C-Cycloalkylmethyl is a methyl radical which is substituted by one of the abovementioned 3–7C-cycloalkyl radicals. Preferably, the 3–5C-cycloalkylmethyl radicals cyclopropylmethyl, cyclobutylmethyl and cyclopentylmethyl may be mentioned.

Phenyl-1–4C-alkyl is one of the abovementioned 1–4C-alkyl radicals which is substituted by phenyl. Examples which may be mentioned are the phenethyl radical and the benzyl radical.

Examples of 1–4C-alkyl which is completely or predominantly substituted by fluorine which may be mentioned are the 2,2,3,3,3-pentafluoropropyl radical, the perfluoroethyl radical, the 1,2,2-trifluoroethyl radical, in particular the 1,1,2,2-tetrafluoroethyl radical, the 2,2,2-trifluoroethyl radical, the trifluoromethyl radical and preferably the difluoromethyl radical.

Halogen within the meaning of the invention is bromine, chlorine and fluorine.

1–4C-Alkoxycarbonyl is a carbonyl group to which one of the abovementioned 1–4C-alkoxy radicals is bonded. Examples which may be mentioned are the methoxycarbonyl radical ($CH_3O$-C(O)—) and the ethoxycarbonyl radical ($CH_3CH_2O$-C(O)—).

1–4C-Alkylcarbonyloxy radicals, in addition to the oxygen atom, contain one of the abovementioned 1–4C-alkylcarbonyl radicals. An example which may be mentioned is the acetoxy radical ($CH_3C(O)O$—).

Mono- or di-1–4C-alkylamino radicals, in addition to the nitrogen atom, contain one or two of the abovementioned 1–4C-alkyl radicals. An example which may be mentioned is the dimethylamino radical.

An example of a 1–4C-alkylcarbonylamino radical which may be mentioned is the propionylamino radical ($C_3H_7C(O)NH$—) and the acetylamino radical ($CH_3C(O)NH$—).

Examples of phenyl radicals substituted by R51, R52 and R53 which may be mentioned are the radicals 2-acetylphenyl, 2-aminophenyl, 2-bromophenyl, 2-chlorophenyl, 2,3-dichlorophenyl, 2,4-dichlorophenyl, 4-diethylamino-2-methylphenyl, 4-bromo-2-trifluoromethylphenyl, 2-carboxy-5-chlorophenyl, 3,5-dichloro-2-hydroxyphenyl, 2-bromo-4-carboxy-5-hydroxyphenyl, 2,6-dichlorophenyl, 2,5-dichlorophenyl, 2,4,6-trichlorophenyl, 2,4,6-trifluorophenyl, 2,6-dibromophenyl, 2-cyanophenyl, 4-cyano-2-fluorophenyl, 2-fluorophenyl, 2,4-difluorophenyl, 2,6-difluorophenyl, 2-chloro-6-fluorophenyl, 2-hydroxyphenyl, 2-hydroxy-4-methoxyphenyl, 2,4-dihydroxyphenyl, 2-methoxyphenyl, 2,3-dimethoxyphenyl, 2,4-dimethoxyphenyl, 2,6-dimethoxyphenyl, 2-dimethylaminophenyl, 2-methylphenyl, 2-chloro-6-methylphenyl, 2,4-dimethylphenyl, 2,6-dimethylphenyl, 2,3-dimethylphenyl, 2-methoxycarbonylphenyl, 2-trifluoromethylphenyl, 2,6-dichloro-4-methoxyphenyl, 2,6-dichloro-4-cyanophenyl, 2,6-dichloro-4-aminophenyl, 2,6-dichloro-4-methoxycarbonylphenyl, 4-acetylamino-2,6-dichlorophenyl and 2,6-dichloro-4-ethoxycarbonylphenyl.

Examples of pyridyl radicals substituted by R54, R55, R56 and R57 which may be mentioned are the radicals 3,5-dichloropyrid-4-yl, 2,6-diaminopyrid-3-yl, 4-aminopyrid-3-yl, 3-methylpyrid-2-yl, 4-methylpyrid-2-yl, 5-hydroxypyrid-2-yl, 4-chloropyrid-3-yl, 3-chloropyrid-2-yl, 3-chloropyrid-4-yl, 2-chloropyrid-3-yl, 2,3,5,6-tetrafluoropyrid-4-yl, 3,5-dichloro-2,6-difluoropyrid-4-yl, 3,5-dibromopyrid-2-yl, 3,5-dibromopyrid-4-yl, 3,5-dichloropyrid-4-yl, 2,6-dichloropyrid-3-yl, 3,5-dimethylpyrod-4-yl, 3-chloro-2,5,6-trifluoropyrid-4-yl and 2,3,5-trifluoropyrid-4-yl.

Suitable salts of compounds of the formula I—depending on substitution—are all acid addition salts or all salts with bases. Particular mention may be made here of the pharmacologically tolerable salts of the inorganic and organic acids customarily used in pharmacy. Those suitable are, on the one hand, water-soluble and water-insoluble acid addition salts with acids such as hydrochloric acid, hydrobromic acid, phosphoric acid, nitric acid, sulfuric acid, acetic acid, citric acid, D-gluconic acid, benzoic acid, 2-(4-hydroxybenzoyl) benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is involved and depending on which salt is desired, in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts which can initially be obtained as process products, for example, in the preparation of the compounds according to the invention on an industrial scale are converted into pharmacologically tolerable salts by processes known to the person skilled in the art.

It is known to the person skilled in the art that the compounds according to the invention and their salts, when they are isolated, for example, in crystalline form, can contain various amounts of solvents. The invention therefore also comprises all solvates and in particular all hydrates of the compounds of the formula I, and also all solvates and in particular all hydrates of the salts of the compounds of the formula I.

Compounds of the formula I to be emphasized are those in which

R1 is 1–4C-alkoxy, 3–5C-cycloalkoxy, 3–5C-cycloalkylmethoxy or 1–4C-alkoxy which is completely or predominantly substituted by fluorine, R2 is hydrogen and R3 is hydrogen, or R2 and R3 together are a methylene group, R4 is hydrogen, 1–6C-alkyl, 1–4C-alkoxy-1–4C-alkyl, 1–4C-alkylthio-1–4C-alkyl, 1–6C-alkylacarbonyl, 3–7C-cycloalkyl, 3–7C-cycloalkylmethyl, phenyl-1–4C-alkyl or 1–4C-alkyl which is completely or predominantly substituted by fluorine, R5 is phenyl, pyridyl, phenyl substituted by R51, R52 and R53 or pyridyl substituted by R54, R55, R56 and R57, where R51 is halogen, cyano, carboxyl, 1–4C-alkyl, 1–4C-alkoxy or 1–4C-alkoxycarbonyl, R52 is hydrogen, halogen, 1–4C-alkyl or 1–4C-alkoxy, R53 is hydrogen, halogen, 1–4C-alkyl or 1–4C-alkoxy, R54 is halogen or 1–4C-alkyl, R55 is hydrogen or halogen,
R56 is hydrogen or halogen and
R57 is hydrogen or halogen,
n is 1 or 2,
m is 1 or 2,
where the sum of m and n may only assume the values 2 or 3, the salts of these compounds and the N-oxides of the pyridines and their salts.

Compounds of the formula I particularly to be emphasized are those in which
R1 is methoxy or difluoromethoxy,
R2 is hydrogen and
R3 is hydrogen
or
R2 and R3 together are a methylene group,
R4 is hydrogen, 1–6C-alkyl, 1–4C-alkoxy-1–4C-alkyl, 1–4C-alkylthio-1–4C-alkyl, 1–4C-alkylcarbonyl, phenethyl or benzyl,
R5 is 2-bromophenyl, 2-chlorophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2-chloro-6-fluorophenyl, 2,6-difluorophenyl, 2,6-dichlorophenyl, 3,5-dichloropyrid-4-yl, 3-methyl-pyrid-2yl, 2-chloropyrid-3-yl, 3-chloropyrid-4-yl, 3,5-dibromopyrid-2-yl, 3,5-difluoropyrid-4-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl
n is 1,
m is 1 and
the salts of these compounds and the N-oxides of the pyridines and their salts.

One embodiment (embodiment a) of the compounds particularly to be emphasized are those compounds of the formula I, in which
R1 is methoxy or difluoromethoxy,
R2 is hydrogen and
R3 is hydrogen,
R4 is hydrogen, 1–6C-alkyl, 1–4C-alkoxy-1–4C-alkyl, 1–4C-alkylthio-1–4C-alkyl, 1–4C-alkylcarbonyl, phenethyl or benzyl,
R5 is 2-bromophenyl, 2-chlorophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2-chloro-6-fluorophenyl, 2,6-difluorophenyl, 2,6-dichlorophenyl, 3,5-dichloropyrid-4-yl, 3-methyl-pyrid-2yl, 2-chloropyrid-3-yl, 3-chloropyrid-4-yl, 3,5-dibromopyrid-2-yl, 3,5-difluoropyrid-4-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl,
n is 1,
m is 1 and
the salts of these compounds and the N-oxides of the pyridines and their salts.

A further embodiment (embodiment b) of the compounds particularly to be emphasized are those compounds of the formula I, in which
R1 is methoxy or difluoromethoxy,
R2 and R3 together are a methylene group,
R4 is hydrogen, 1–6C-alkyl, 1–4C-alkoxy-1–4C-alkyl, 1–4C-alkylthio-1–4C-alkyl, 1–4C-alkylcarbonyl, phenethyl or benzyl,
R5 is 2-bromophenyl, 2-chlorophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2-chloro-6-fluorophenyl, 2,6-difluorophenyl, 2,6-dichlorophenyl, 3,5-dichloropyrid-4-yl, 3-methylpyrid-2-yl, 2-chloropyrid-3-yl, 3-chloropyrid-4-yl, 3,5-dibromopyrid-2-yl, 3,5-difluoropyrid-4-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl,
n is 1,
m is 1 and
the salts of these compounds and the N-oxides of the pyridines and their salts.

Preferred compounds of the formula I are those in which
R1 is methoxy or difluoromethoxy,
R2 is hydrogen and
R3 is hydrogen,
or
R2 and R3 together are a methylene group,
R4 is hydrogen, 1–4C-alkyl, 1–2C-alkoxy-1–2C-alkyl, 1–2C-alkylthio-1–2C-alkyl, 1–4C-alkylcarbonyl or benzyl,
R5 is 3,5-dichloropyrid-4-yl, 2-chloropyrid-3-yl, 3-chloropyrid-4-yl, 3,5-dibromopyrid-2yl, 3,5-difluoropyrid-4-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl,
n is 1,
m is 1 and
the salts of these compounds and the N-oxides of the pyridines and their salts.

Preferred compounds of the formula I of embodiment a are those in which
R1 is methoxy or difluoromethoxy,
R2 is hydrogen and
R3 is hydrogen,
R4 is hydrogen, 1–4C-alkyl, 1–2C-alkoxy-1–2C-alkyl, 1–2C-alkylthio-1–2C-alkyl or benzyl,
R5 is 3,5-dichloropyrid-4-yl, 2-chloropyrid-3-yl, 3-chloropyrid-4-yl, 3,5-dibromopyrid-2-yl, 3,5-difluoropyrid-4-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl,
n is 1,
m is 1 and
the salts of these compounds and the N-oxides of the pyridines and their salts.

Preferred compounds of the formula I of embodiment b are those in which
R1 is methoxy or difluoromethoxy,
R2 and R3 together are a methylene group,
R4 is hydrogen, 1–4C-alkyl or benzyl,
R5 is 3,5-dichloropyrid-4-yl, 2-chloropyrid-3-yl, 3-chloropyrid-4-yl, 3,5-dibromopyrid-2-yl, 3,5-difluoropyrid-4-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl,
n is 1,
m is 1 and
the salts of these compounds and the N-oxides of the pyridines and their salts.

Particularly preferred compounds of the formula I are those in which

R1 is methoxy,
R2 is hydrogen and
R3 is hydrogen, or

R2 and R3 together are a methylene group,
R4 is hydrogen, methyl, ethyl, methylthiomethyl or benzyl,
R5 is 3,5-dichloropyrid-4-yl,
n is 1,
m is 1 and the salts of these compounds.

Particularly preferred compounds of the formula I of embodiment a are those in which R1 is methoxy,
R2 is hydrogen and
R3 is hydrogen,
R4 is hydrogen, methyl, ethyl, methylthiomethyl or benzyl,
R5 is 3,5-dichloropyrid-4-yl,
n is 1,
m is 1 and the salts of these compounds.

Particularly preferred compounds of the formula I of embodiment b are those in which R1 is methoxy,
R2 and R3 together are a methylene group,
R4 is methyl or benzyl,
R5 is 3,5-dichloropyrid-4-yl,
n is 1,
m is 1 and the salts of these compounds.

The compounds of the formula I are chiral compounds. Chiral centers occur on the carbon atoms bonded to the substituents (groups) R3 and OR4.

The invention comprises both the pure enantiomers and their mixtures in any mixing ratio, including the racemates. The enantiomers can be separated in a known manner, for example by preparation and separation of corresponding diastereomeric compounds.

If R2 and R3 together form a methylene group, a spiro compound is present.

The invention further relates to processes for the preparation of the compounds of the formula I and their salts, and also of the N-oxides of the pyridines and their salts.

The first process is characterized in that compounds of the formula II

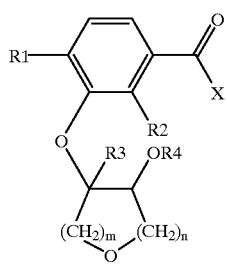

(II)

in which R1, R2, R3, R4, m and n have the meanings indicated above and X is a suitable leaving group, are reacted with amines R5-NH$_2$, and in that, if desired, compounds of the formula I obtained are then converted into their salts and/or pyridines obtained are converted into the N-oxides and, if desired, then into the salts. or in that, if desired, salts of the compounds of the formula I obtained are then converted into the free compounds.

The person skilled in the art is familiar on the basis of his/her expert knowledge with which leaving groups X are suitable. For example, suitable acid halides of the formula II (X=Cl or Br) are used as starting materials. Otherwise, the reaction is carried out, for example, as described in the following examples or in a manner familiar per se to the person skilled in the art (e.g. as described in the international patent applications WO 95/01338 or WO96/03399).

The N-oxidation is carried out in a manner likewise familiar to the person skilled in the art, e.g. with the aid of m-chloroperoxibenzoic acid in dichloromethane at room temperature. The reaction conditions which are specifically necessary for carrying out the process are known to the person skilled in the art on the basis of his/her expert knowledge.

The compounds of the formula II can be prepared according to the general reaction scheme 1.

Reaction scheme 1

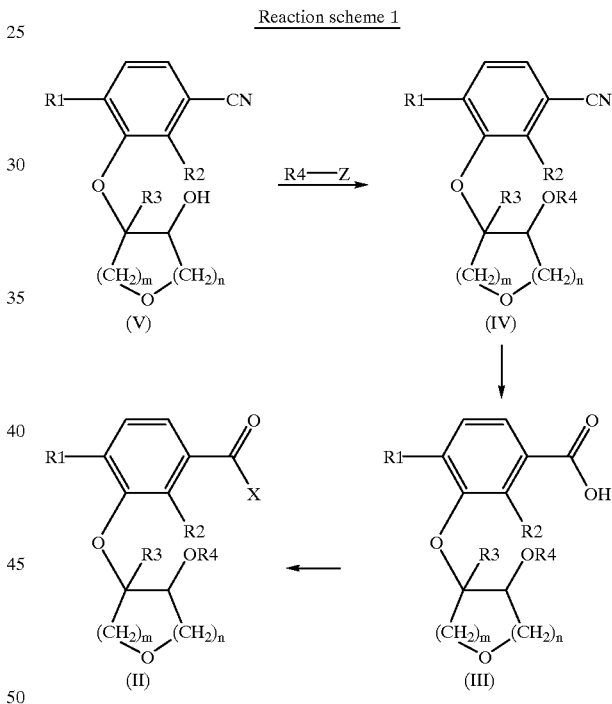

In a first reaction step, the compounds of the formula V, in which R1, R2, R3, m and n have the meanings indicated above are subjected to an alkylation reaction.

The alkylation is carried out in a suitable inert solvent such as DMF, THF or DMSO with addition of a base, preferably sodium hydride, and an alkylating reagent of the formula R4-Z, in which R4 has the meanings indicated above (exception R4≠H) and Z is a suitable leaving group.

The cyano group is then hydrolyzed to the carboxyl group (compounds of the formula III) in the compounds of the formula IV obtained by methods known to the person skilled in the art. The final activation of the carboxyl group (for example by conversion into an acid halide) yields the starting compounds of the formula II.

By way of example, the preparation of compounds of the formula II is described in the following examples under "starting compounds". The preparation of further compounds of the formula II can be carried out in an analogous manner.

The amines R5-NH$_2$ are known, or they can be prepared in a known manner.

Compounds of the formula V can be prepared according to the general reaction scheme 2:

example, in Larock, Comprehensive Organic Transformations pp. 479–480 (VCH 1989).

The second process which preferably for the preparation of compounds of the formula I, in which R1, R5, m and n have the meanings indicated above and R2, R3 and R4 are hydrogen is characterized in that compounds of the formula X

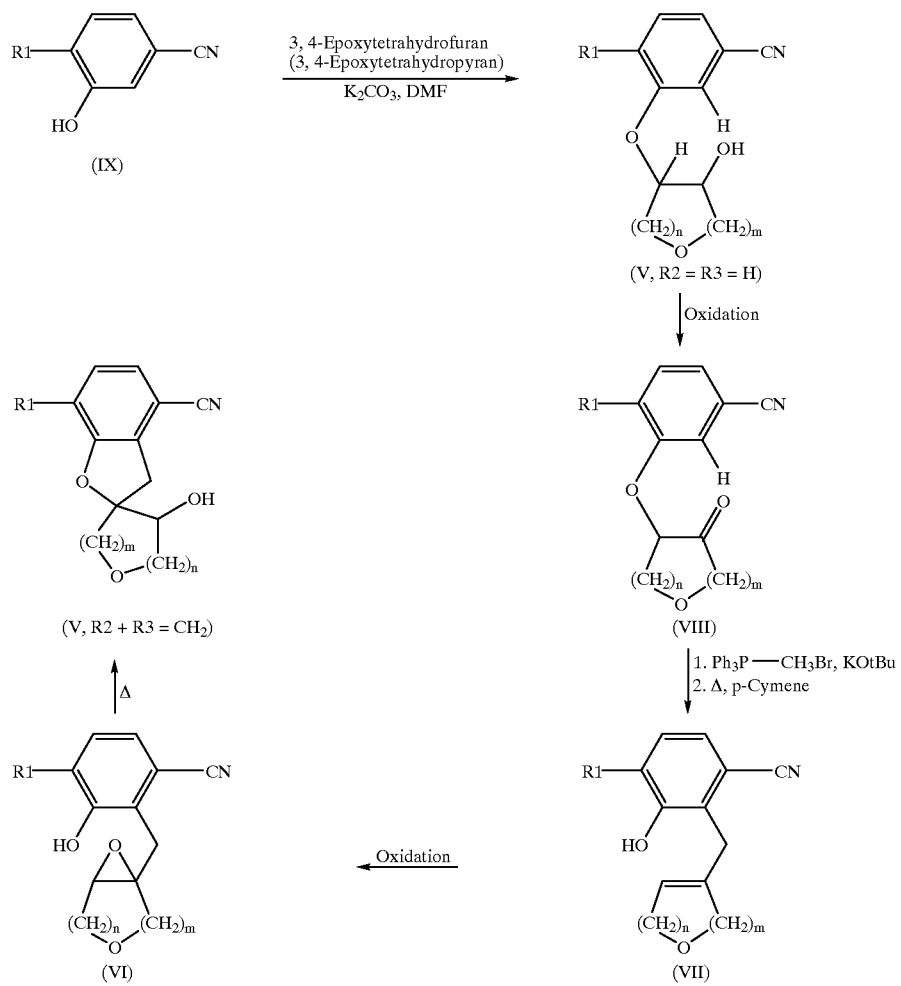

The preparation of compounds of the formula V (R2=R3=H or R2+R3=CH$_2$), in which R1, m and n have the meanings indicated above is described by way of example in the following examples under "starting compounds". The preparation of further compounds of the formula V can be carried out in an analogous manner.

In the compounds of the formula V (R2=R3=H and R2+R3=CH$_2$) prepared according to reaction scheme 2, the substituents of the chiral centers are preferably in the trans configuration.

Corresponding compounds of the formula V (R2=R3=H and R2+R3=CH$_2$) in which the substituents on the chiral centers are in the cis configuration can be prepared by configuration inversion reactions known to the person skilled in the art. Such reactions are described, for

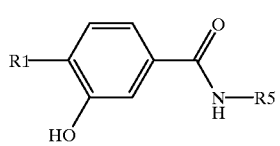

(X)

are reacted with 3,4-epoxytetrahydrofuran or 3,4-epoxytetrahydropyran and that, if desired, compounds of the formula I obtained are converted into their salts and/or pyridines obtained are converted into the N-oxides and, if desired, then converted into the salts, or in that, if desired, salts of the compounds of the formula I obtained are then converted into the free compounds.

The reaction can be carried out, for example, in DMF as a solvent with addition of potassium carbonate as a base, preferably at elevated temperature.

Compounds of the formula X can be prepared, for example, according to general reaction scheme 3 with or without introduction of a temporary protective group (TP) on the phenolic hydroxyl group.

Reaction scheme 3

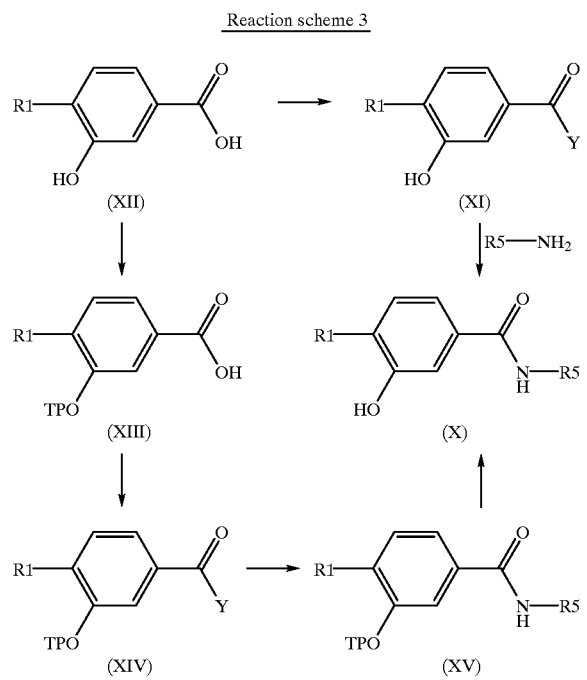

Here, a suitable leaving group Y (e.g. Y=Cl or Br) is first introduced in the case of the compounds of the formula XII. The compounds of the formula XI obtained are then reacted with amines of the formula R5-NH$_2$ to give the compounds of the formula X. Alternatively, the preparation of the compounds of the formula X can also be carried out via the temporarily protected compounds of the formulae XIII, XIV and XV.

Compounds of the formula XII are known, commercially available or can be prepared according to known processes.

Compounds of the formula I, in which R1, R2, R3, R5, m and n have the meanings indicated above and R4 is hydrogen can also be prepared according to the process described first by introducing a temporary protective group instead of the substituent R4 and removing this group again at the end of the reaction sequence.

It is known to the person skilled in the art that if there are a number of reactive centers on a starting compound or intermediate, it may be necessary to temporarily block one or more reactive centers by protective groups in order to allow a reaction to proceed specifically at the desired reaction center. A detailed description of the use of a large number of proven protective groups is found, for example, in T. W. Greene, Protective Groups in Organic Synthesis, John Wiley & Sons, 1991.

The isolation and purification of the substances according to the invention is carried out in a manner known per se, for example by distilling off the solvent in vacuo and recrystallizing the residue obtained from a suitable solvent or subjecting it to one of the customary purification methods, such as column chromatography on suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular weight aliphatic alcohol such as ethanol or isopropanol), which contains the desired acid or base, or to which the desired acid or base is then added. The salts are obtained by filtration, reprecipitation, precipitation with a nonsolvent for the addition salt or by evaporation of the solvent. Salts obtained can be converted by alkalization or by acidification into the free compounds, which in turn can be converted into salts. In this way, pharmacologically intolerable salts can be converted into pharmacologically tolerable salts.

The following examples serve to illustrate the invention in greater detail without restricting it. Likewise, further compounds of the formula I whose preparation is not described explicitly can be prepared in an analogous manner or in a manner familiar per se to the person skilled in the art using customary process techniques.

In the examples, m.p. stands for melting point, d for day(s), h for hour(s), min for minute(s) and RT for room temperature. The invention preferably relates to the compounds mentioned in the examples and their salts.

EXAMPLES

Final Compounds:

1. N-(3,5-Dichloropyridin-4-yl)-4-methoxy-3-(4-methoxytetrahydrofuran-3-yloxy)benzamide 1.0 g (3.7 mmol) of 4-methoxy-3-(4-methoxytetrahydrofuran-3-yloxy)benzoic acid (starting compound A1) is heated to reflux for 2 h in 4 ml of oxalyl chloride. Excess oxalyl chloride is removed in vacuo and coevaporated using 2×20 ml of toluene. A solution of 600 mg (3.7 mmol) of 4-amino-3,5-dichloropyridine in 10 ml of tetrahydrofuran is added dropwise to a suspension of 220 mg (7.4 mmol) of 80% strength sodium hydride in 10 ml of tetrahydrofuran. The mixture is stirred for 1 h at RT, the acid chloride is then added dropwise in a further 10 ml of tetrahydrofuran and the reaction mixture is stirred at RT overnight. It is concentrated, the residue is treated with 50 ml of water and the mixture is extracted with 3×50 ml of dichloromethane. The combined organic phases are dried over magnesium sulfate, concentrated and the residue is crystallized from 50 ml of isopropanol. 1.2 g of the title compound of m.p. 175–177° C. are obtained.

2. N-(3,5-Dichloropyridin-4-yl)-3-(4-ethoxytetrahydrofuran-3-yloxy)-4-methoxybenzamide 1.0 g (3.5 mmol) of 3-(4-ethoxytetrahydrofuran-3-yloxy)-4-methoxybenzoic acid (starting compound A2) are reacted analogously to example 1 and 1.0 g of the title compound of m.p. 171–173° C. is obtained.

3. N-(3,5-Dichloropyridin-4-yl)-3-(4-benzyloxytetrahydrofuran-3-yloxy)-4-methoxybenzamide 1.0 g (2.9 mmol) of 3-(4-benzyloxytetrahydrofuran-3-yloxy)-4-methoxybenzoic acid (starting compound A3) are reacted analogously to example 1 and 1.17 g of the title compound of m.p. 190–191° C. are obtained.

4. N-(3,5-Dichloropyridin-4-yl)-2,3-dihydro-4',7-dimethoxybenzofuran-2-spiro-3'-tetrahydro-furan-4-carboxamide 700 mg (2.5 mmol) of 2,3-dihydro-4'7-dimethoxybenzofuran-2-spiro-3'-tetrahydrofuran-4-carboxylic acid (starting compound A4) are heated to reflux for 2 h in 10 ml of oxalyl chloride. Excess oxalyl chloride is removed in vacuo and coevaporated using 2×10 ml of toluene. A solution of 900 mg (5.5 mmol) of 4-amino-3,5-dichloropyridine in 10 ml of tetrahydrofuran is added dropwise to a suspension of 220 mg (5.5 mmol) of 60% strength sodium hydride in 5 ml of tetrahydrofuran. The mixture is stirred at RT for 3 h, the acid chloride is then added dropwise in a further 15 ml of tetrahydrofuran and the reaction mixture is stirred at RT overnight. It is concentrated, the residue is treated with 50 ml of water and the mixture is extracted with 3×50 ml of dichloromethane. The combined organic phases are dried over magnesium sulfate, concentrated and the residue is chromatographed on silica gel [toluene/ethyl acetate/acetic acid=20:10:1]. The product-containing fractions are concentrated and the residue is crystallized from a water/methanol mixture. 730 mg of the title compound of m.p. 98° C. [sintering] are obtained.

5. N-(3,5-Dichloropyridin-4-yl)-2,3-dihydro-4'-benzyloxy-7-methoxybenzofuran-2-spiro-3'-tetrahydrofuran-4-carboxamide 400 mg (1.12 mmol) of 2,3-dihydro-4'-benzyloxy-7-methoxybenzofuran-2-spiro-3'-tetrahydrofuran-4-carboxylic acid (starting compound A5) are heated to reflux for 90 min in 3 ml of oxalyl chloride. Excess oxalyl chloride is removed in vacuo and coevaporated using 2×10 ml of toluene. A solution of 400 mg (2.5 mmol) of 4-amino-3,5-dichloropyridine in 10 ml of tetrahydrofuran is added dropwise to a suspension of 100 mg (2.5 mmol) of 60% strength sodium hydride in 3 ml of tetrahydrofuran. The mixture is stirred at RT for 90 min, then the acid chloride is added dropwise in a further 5 ml of tetrahydrofuran and the reaction mixture is stirred at RT for 2 h. It is concentrated, the residue is treated with 50 ml of water and the mixture is extracted with 3×50 ml of dichloromethane. The combined organic phases are dried over magnesium sulfate, concentrated and the residue is chromatographed on silica gel [toluene/ethyl acetate=4:1]. The product-containing fractions are concentrated and the residue is crystallized from diisopropyl ether. 270 mg of the title compound of m.p. 82–84° C. are obtained.

6. N-(3,5-Dichloropyridin-4-yl)-3-(4-hydroxytetrahydrofuran-3-yloxy)-4-methoxybenzamide 400 mg (1.2 mmol) of N-(3,5-dichloropyridin-4-yl)-3-hydroxy-4-methoxybenzamide (starting compound A16) and 540 mg (3.85 mmol) of potassium carbonate are stirred under a nitrogen atmosphere at RT for 1 h in 5 ml of dimethylformamide. The mixture is heated to 120° C. and 115 mg (1.3 mmol) of 3,4-epoxytetrahydrofuran are added to the reaction mixture 4×at an interval of 6 h in each case. The mixture is concentrated, 50 ml of water are added, it is acidified with 2 N HCl and extracted with 3×50 ml of ethyl acetate. The combined organic phases are washed with saturated sodium chloride solution, dried over magnesium sulfate, concentrated and the residue is chromatographed on silica gel [toluene/ethyl acetate=1:2]. The product-containing fractions are concentrated and the residue is crystallized from diethyl ether. 130 mg of the title compound of m.p. 183–185° C. are obtained.

7. N-(3,5-Dichloropyridin-4-yl)-4-methoxy-3-(4-methylthiomethyloxytetrahydrofuran-3-yloxy)-benzamide 1.0 g (3.2 mmol) of 4-methoxy-3-(4-methylthiomethyloxytetrahydrofuran-3-yloxy)benzoic acid (starting compound A19) are heated to reflux for 90 min in 4 ml of oxalyl chloride. Excess oxalyl chloride is removed in vacuo and coevaporated using 2×20 ml of toluene. A solution of 520 mg (3.2 mmol) of 4-amino-3,5-dichloropyridine in 10 ml of tetrahydrofuran is added dropwise to a suspension of 200 mg (6.9 mmol) of 80% strength sodium hydride in 10 ml of tetrahydrofuran. The mixture is stirred at RT for 90 min, then the acid chloride is added dropwise in a further 10 ml of tetrahydrofuran and the reaction mixture is stirred at RT for 2 h. It is concentrated, the residue is treated with 25 ml of water and the mixture is extracted with 3×25 ml of ethyl acetate. The combined organic phases are washed with saturated sodium chloride solution, dried over magnesium sulfate, concentrated and the residue is chromatographed on silica gel. The product-containing fractions are concentrated and the residue is crystallized from acetonitrile. 300 mg of the title compound of m.p. 195–198° C. are obtained.

Starting Compounds:

A1. 4-Methoxy-3-(4-methoxytetrahydrofuran-3-yloxy)benzoic acid 2.0 g (8.0 mmol) of 4-methoxy-3-(4-methoxytetrahydrofuran-3-yloxy)benzonitrile (A6) and 4.2 g (80.0 mmol) of potassium hydroxide are heated at 140° C. for 3 h in 20 ml of glycerol. The mixture is treated with 50 ml of water and acidified by dropwise addition of 40 ml of 2 N hydrochloric acid with ice-cooling. It is subsequently stirred for 1 h, filtered and the precipitate is washed with ice water. 1.79 g of the title compound of m.p. 166–168° C. are obtained.

A2. 3-(4-Ethoxytetrahydrofuran-3-yloxy)-4-methoxybenzoic acid 1.46 g (5.5 mmol) of 3-(4-ethoxytetrahydrofuran-3-yloxy)-4-methoxybenzonitrile (A7) and 3.0 g (55.0 mmol) of potassium hydroxide are heated at 140° C. for 3 h in 15 ml of glycerol. The mixture is treated with 50 ml of water, washed with 2×25 ml of ethyl acetate and the aqueous phase is acidified by dropwise addition of 30 ml of 2 N hydrochloric acid with ice-cooling. The mixture is subsequently stirred for 1 h, filtered and the precipitate is washed with ice water. 1.49 g of the title compound of m.p. 135–138° C. are obtained.

A3. 3-(4-Benzyloxytetrahydrofuran-3-yloxy)-4-methoxybenzoic acid 2.8 g (8.6 mmol) of 3-(4-benzyloxytetrahydrofuran-3-yloxy)-4-methoxybenzonitrile (A8) and 4.8 g (86.0 mmol) of potassium hydroxide are heated at 140° C. for 3 h in 30 ml of glycerol. The mixture is treated with 70 ml of water and acidified by dropwise addition of 40 ml of 2 N hydrochloric acid with ice-cooling. The mixture is subsequently stirred for 1 h, filtered and the precipitate is washed with ice water. For further purification, the product is chromatographed on silica gel [toluenelethyl acetate =2:1]. The product-containing fractions are concentrated and the residue is crystallized from isopropanol. 2.1 g of the title compound of m.p. 153–156° C. are obtained.

A4. 2,3-Dihydro-4',7-dimethoxybenzofuran-2-spiro-3'-tetrahydrofuran-4-carboxylic acid 1.95 g (7.5 mmol) of 2,3-dihydro-4-cyano-4',7-dimethoxybenzofuran-2-spiro-3'-tetrahydrofuran (A9 ) and 4.2 g (75.0 mmol) of potassium hydroxide are heated at 140° C. for 3 h in 40 ml of glycerol. The mixture is treated with 150 ml of water and acidified by dropwise addition of 30 ml of 2 N hydrochloric acid with ice-cooling. It is subsequently stirred for 1 h, filtered and the precipitate is washed with ice water. 1.97 9 of the title compound of m.p. 231–232° C. are obtained.

A5. 2,3-Dihydro-4'-benzyloxy-7-methoxybenzofuran-2-spiro-3'-tetrahydrofuran-4-carboxylic acid 650 mg (1.92 mmol) of 2,3-dihydro-4'-benzyloxy-4-cyano-7-methoxybenzofuran-2-spiro-3'-tetrahydrofuran (A10) and 1.35 g (19 mmol) of potassium hydroxide are heated at 150° C. for 5 h in 15 ml of glycerol. The mixture is treated with 40 ml of water and acidified by dropwise addition of 10 ml of 2 N hydrochloric acid with ice-cooling. The mixture is subsequently stirred for 1 h, filtered and the precipitate is washed with ice water. 610 mg of the title compound of m.p. 196–198° C. are obtained.

A6. 4-Methoxy-3-(4-methoxytetrahydrofuran-3-yloxy) benzonitrile 1.0 g (4.2 mmol) of 3-(4-hydroxytetrahydrofuran-3-yloxy)-4-methoxybenzonitrile (A15) in 5 ml of dimethylformamide is added dropwise under a nitrogen atmosphere to a solution of 140 mg (4.6 mmol) of 80% strength sodium hydride in 5 ml of dimethylformamide and the mixture is heated at 60° C. for 20 min. 315 µl (5.0 mmol) of methyl iodide, dissolved in 1 ml of dimethylformamide, are then added dropwise at RT. The mixture is stirred at RT for 2 h, concentrated, treated with 20 ml of water and acidified with 2 N hydrochloric acid. After extraction with 3×30 ml of ethyl acetate, the combined organic phases are dried over magnesium sulfate, concentrated and the crude product is recrystallized from 10 ml of isopropanol. 760 mg of the title compound of m.p. 98–100° C. are obtained.

A7. 3-(4-Ethoxytetrahydrofuran-3-yloxy)-4-methoxybenzonitrile 1.0 g (4.2 mmol) of 3-(4-hydroxytetrahydrofuran-3-yloxy)-4-methoxybenzonitrile (A15) in 5 ml of dimethylformamide are added dropwise under a nitrogen atmosphere to a solution of 140 mg (4.6 mmol) of sodium hydride in 5 ml of dimethylformamide and the mixture is heated at 40° C. for 1 h. 600 µl (7.5 mmol) of ethyl iodide, dissolved in 1 ml of dimethylformamide, are then added dropwise at RT. The mixture is stirred at RT for 2 h, concentrated, treated with 25 ml of water and acidified with 2 N hydrochloric acid. After extraction with 3×25 ml of ethyl acetate, the combined organic phases are washed with saturated sodium chloride solution, dried over magnesium sulfate and concentrated. For further purification, the product is chromatographed on silica gel [toluene/ethyl acetate=4:1]. The product-containing fractions are concentrated and the residue is crystallized from isopropanol. 660 mg of the title compound of m.p. 64–66° C. are obtained.

A8. 3-(4-Benzyloxytetrahydrofuran-3-yloxy)-4-methoxybenzonitrile 2.5 g (11.0 mmol) of 3-(4-hydroxytetrahydrofuran-3-yloxy)-4-methoxybenzonitrile (A 15) in 12 ml of dimethylformamide are added dropwise under a nitrogen atmosphere to a solution of 350 mg (12.0 mmol) of sodium hydride in 12 ml of dimethylformamide and the mixture is heated at 40° C. for 1 h. 1.6 ml (13.0 mmol) of benzyl chloride, dissolved in 6 ml of dimethylformamide, are then added dropwise at RT. The mixture is stirred at RT for 4 h. concentrated, treated with 50 ml of water and acidified with 2 N hydrochloric acid. After extraction with 3×40 ml of ethyl acetate, the combined organic phases are washed with saturated sodium chloride solution, dried over magnesium sulfate and concentrated. For further purification, the product is chromatographed on silica gel [toluene/ethyl acetate=4:1]. The product-containing fractions are concentrated and the residue is crystallized from isopropanol. 3.05 g of the title compound of m.p. 72–75° C. are obtained.

A9. 2,3-Dihydro-4-cyano-4',7-dimethoxybenzofuran-2-spiro-3'-tetrahydrofuran 2.0 g (8.0 mmol) of 2,3-dihydro-4-cyano-4'-hydroxy-7-methoxybenzofuran-2-spiro-3'-tetrahydrofuran (A11) in 15 ml of dimethylformamide are added dropwise under a nitrogen atmosphere to a solution of 270 mg (8.8 mmol) of 80% strength sodium hydride in 10 ml of dimethylformamide and the mixture is heated at 40° C. for 1 h. 700 µl (10.6 mmol) of methyl iodide, dissolved in 5 ml of dimethylformamide, are then added dropwise at RT. The mixture is stirred at RT for 2 h, concentrated, and the residue is crystallized from 50 ml of water. 1.97 g of the title compound of m.p. 151–156° C. are obtained.

A10. 2,3-Dihydro-4'-benzyloxy-4-cyano-7-methoxybenzofuran-2-spiro-3'-tetrahydrofuran 750 mg (3.03 mmol) of 2,3-dihydro-4-cyano-4'-hydroxy-7-methoxybenzofuran-2-spiro-3'-tetrahydrofuran (A11) in 10 ml of dimethylformamide are added dropwise under a nitrogen atmosphere to a solution of 110 mg (3.65 mmol) of 80% strength sodium hydride in 2 ml of dimethylformamide and the mixture is heated at 40° C. for 90 min. 470 µl (10.6 mmol) of benzyl bromide, dissolved in 10 ml of dimethylformamide, are then added dropwise. The mixture is stirred at RT for 4 h, concentrated and treated with 25 ml of water. After extraction with 3×25 ml of ethyl acetate, the combined organic phases are dried over magnesium sulfate and concentrated. For further purification, the product is chromatographed on silica gel [toluene/ethyl acetate=9:1]. The product-containing fractions are concentrated and the residue is crystallized from diisopropyl ester 740 mg of the title compound of m.p. 146–147° C. are obtained.

A11. 2,3-Dihydro-4-cyano-4'-hydroxy-7-methoxybenzofuran-2-spiro-3'-tetrahydrofuran 2.3 g (9.5 mmol) of 2-(3,4-epoxytetrahydrofuran-3-ylmethyl)-3-hydroxy-4-methoxybenzonitrile (A12) are heated at 140° C. for 3 h. The product is crystallized from hot methanol and 1.7 g of the title compound of m.p. 171–176° C. are obtained.

A12. 2(3,4-Epoxytetrahydrofuran-3-ylmethyl)-3-hydroxy-4-methoxybenzonitrile 2.3 g (10.0 mmol) of 2-(2,5-dihydrofuran-3-ylmethyl)-3-hydroxy-4-methoxybenzonitrile (A13) and 2.7 g (11 mmol) of 70–75% strength m-chloroperbenzoic acid are stirred overnight at RT in 50 ml of dichloromethane. The reaction mixture is washed successively with saturated sodium hydrogencarbonate solution, sodium disulfite solution and sodium chloride solution, dried over magnesium sulfate and the organic phase is concentrated. The crude product is reacted without further purification.

A13. 2-(2,5-Dihydrofuran-3-ylmethyl)-3-hydroxy-4-methoxybenzonitrile 46.4 g (128.0 mmol) of methyltriphenylphosphonium bromide and 14.6 g (128.0 mmol) of potassium t-butoxide are stirred under a nitrogen atmosphere at RT for 3 h in 300 ml of tetrahydrofuran. The mixture is cooled to 0° C., 25.3 g (108.0 mmol) of 3-(tetrahydrofuran-4-on-3-yloxy)-4-methoxybenzonitrile (A14) in 200 ml of tetrahydrofuran are added and the mixture is stirred with ice-cooling for 4 h. It is then largely concentrated and hydrolyzed with 300 ml of water. The mixture is extracted with a total of 900 ml of ethyl acetate, the combined organic phases are dried over magnesium sulfate and concentrated. The crude product is filtered through silica gel [toluene/ethyl acetate=4:1] and then heated at 150° C. for 8 h in 400 ml of p-cymene. The product crystallizes from the reaction mixture on cooling and 17.75 g of the title compound of m.p. 142–144° C. are obtained.

A14. 3-(Tetrahydrofuran-4-on-3-yloxy)-4-methoxybenzonitrile 2.05 ml (25.5 mmol) of pyridine and 1.2 ml (12.75 mmol) of acetic anhydride are added dropwise at 0° C. to a solution of 1.27 [lacuna] (12.75 mmol) of chromium(VI) oxide in 50 ml of dichloromethane. After 15 min at RT, 1.0 g (4.25 mmol) of 3-(4-hydroxytetrahydrofuran-3-yloxy)-4-methoxybenzonitrile (A15) in 25 ml of dichloromethane is added dropwise. The reaction mixture is stirred at RT for 1 h and then filtered through Celite. The filtrate is treated with water and acidified with 2 N hydrochloric acid. The phases are separated, the aqueous phase is extracted with dichloromethane, the combined organic phases are dried over magnesium sulfate and concentrated. For further purification, the product is chromatographed on silica gel [ethyl acetate]. The product-containing fractions are concentrated and the residue is crystallized from diisopropyl ether. 730 mg of the title compound of m.p. 147–149° C. are obtained.

A15. 3-(4-Hydroxytetrahydrofuran-3-yloxy)-4-methoxybenzonitrile 50 g (335 mmol) of 3-hydroxy-4-methoxybenzonitrile and 92 g (670 mmol) of potassium carbonate are suspended in 900 ml of dimethylformamide and the mixture is stirred at RT for 1 h. 32 g (368 mmol) of 3,4-epoxytetrahydrofuran are then added dropwise and the mixture is stirred at 90° C. for 6 h. The solvent is evaporated in vacuo and the residue is partitioned between 500 ml of ethyl acetate and 500 ml of water. The phases are separated, the aqueous phase is extracted with 4×250 ml of ethyl acetate, the combined organic phases are washed with saturated sodium chloride solution, dried over magnesium sulfate and concentrated. The crude product is recrystallized in 400 ml of toluene. 62 g of the title compound of m.p. 147–149° C. are obtained.

A16. N-(3,5-Dichloropyridin-4-yl)-3-hydroxy-4-methoxybenzamide

A suspension of 1.0 g (2.5 mmol) of N-(3,5-dichloropyridin-4-yl)-4-methoxy-3-pivaloyloxybenzamide (A17) in 5 ml of methanol is treated with 325 mg (6.0 mmol) of sodium methoxide in 5 ml of methanol and heated at 50° C. for 4 h. It is allowed to cool, concentrated, treated with 50 ml of water, acidified with 2 N hydrochloric acid and extracted with 4×50 ml of ethyl acetate. The combined organic phases are dried over magnesium sulfate, concentrated and the crude product is crystallized from 20 ml of isopropanol. 870 mg of the title compound of m.p. 231–233° C. are obtained.

A17. N-(3,5-Dichloropyridin-4-yl)-4-methoxy-3-pivaloyloxybenzamide 1.0 g (4.0 mmol) of 4-methoxy-3-pivaloyloxybenzoic acid (A18) are heated to reflux for 2 h in 10 ml oxalyl chloride. Excess oxalyl chloride is removed in vacuo and coevaporated using 2×20 ml of toluene. A solution of 650 mg (4.0 mmol) of 4-amino-3,5-dichloropyridine in 10 ml of tetrahydrofuran is added dropwise to a suspension of 240 mg (8.0 mmol) of 80% strength sodium hydride in 10 ml of tetrahydrofuran. The mixture is stirred at RT for 1 h, then the acid chloride is added dropwise in a further 10 ml of tetrahydrofuran and the reaction mixture is stirred at RT for 3 h. It is concentrated, the residue is treated with 20 ml of water and 20 ml of saturated sodium chloride solution and extracted with 3×50 ml of ethyl acetate. The combined organic phases are dried over magnesium sulfate, concentrated and the crude product is recrystallized from 15 ml of diisopropyl ether. 1.29 g of the title compound of m.p. 177–179° C. are obtained.

A18. 4-Methoxy-3-pivaloyloxybenzoic acid 2.0 g (12.0 mmol) of isovanillic acid are dissolved in 15 ml of pyridine and 15 ml of toluene and treated with 3.8 ml (32.0 mmol) of pivaloyl chloride. The mixture is stirred at RT for 48 h. The reaction mixture is then treated with 20 ml of 2 N sodium hydroxide solution and heated to reflux for 1 h. It is then allowed to cool, acidified with semiconcentrated hydrochloric acid to pH=1 and extracted with 2×50 ml of toluene. The combined organic phases are dried over magnesium sulfate, concentrated and the product is crystallized from 25 ml of toluene. 1.1 g of the title compound of m.p.182–183° C. are obtained.

A19. 4-Methoxy-3-(4-methylthiomethyloxytetrahydrofuran-3-yloxy)benzoic acid 6.5 g (22.0 mmol) of 4-methoxy-3-(4-methylthiomethyloxytetrahydrofuran-3-yloxy)benzonitrile (A20) and 12.3 g (220 mmol) of potassium hydroxide are heated at 130° C. for 3 h in 60 ml of glycerol. The mixture is then treated with 100 ml of water and acidified to pH=5 by dropwise addition of 2 N hydrochloric acid. It is extracted with a total of 900 ml of ethyl acetate, the combined organic phases are dried over magnesium sulfate, concentrated and the residue is stirred in hot ethyl acetate. After recrystallization from isopropanol, 5.15 g of the title compound of m.p. 144–145° C. are obtained.

A20. 4-Methoxy-3-(4-methylthiomethyloxytetrahydrofuran-3-yloxy) benzonitrile 31.0 g (132 mmol) of 3-(4-hydroxytetrahydrofuran-3-yloxy)-4-methoxybenzonitrile (A15) are stirred at RT for 2 d in 500 ml of acetic anhydride and 180 ml of dimethyl sulfoxide. The mixture is concentrated and the residue is recrystallized from 300 ml of isopropanol. The crude product is again recrystallized from 500 ml of ethanol. 6.6 g of the title compound of m.p. 124–125° C. are obtained.

COMMERCIAL APPLICABILITY

The compounds according to the invention have valuable pharmacological properties which make them commercially utilizable. As selective cyclic nucleotide phosphodiesterase (PDE) inhibitors (namely of type 4), they are suitable on the one hand as bronchial therapeutics (for the treatment of airway obstructions on account of their dilating but also on account of their respiratory rate- or respiratory drive-increasing action) and for the elimination of erectile dysfunction on account of the vasodilating action, but on the other hand especially for the treatment of disorders, in particular of inflammatory nature, e.g. of the airways (asthma prophylaxis), of the skin, of the central nervous system, of the intestine, of the eyes and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen radicals and proteases. The compounds according to the invention are distinguished here by low toxicity, good enteral absorption (high bioavailability), a large therapeutic breadth and the absence of significant side-effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of various origins (bronchitis, allergic bronchitis, bronchial asthma, emphysema, COPD); dermatoses (especially of proliferative, inflammatory and allergic type) such as, for example, psoriasis (vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and wide-area pyodermias, endogenous and exogenous acne, acne rosacea and other proliferative, inflammatory and allergic skin disorders; disorders which are based on an excessive release of TNF and leukotrienes, e.g. disorders of the arthritis type (rheumatoid arthritis, rheumatoid spondylitis, osteoarthritis and other arthritic conditions), disorders of the immune system (AIDS, multiple sclerosis), graft-versus-host reactions, transplant rejection reactions, symptoms of shock [septic shock, endotoxin shock, gram-negative sepsis, toxic shock syndrome and ARDS (adult respiratory distress syndrome)], and generalized inflammations in the gastrointestinal area (Crohn's disease and ulcerative colitis); disorders which are based on allergic and/or chronic, faulty immunological reactions in the area of the upper airways (pharynx, nose) and the adjacent regions (paranasal sinuses, eyes), such as, for example, allergic rhinitis/sinusitis, chronic rhinitis/sinusitis, allergic conjunctivitis and nasal polyps; but also disorders of the heart which can be treated by PDE inhibitors, such as, for example, cardiac insufficiency, or disorders which can be treated on account of the tissue-relaxant action of the PDE inhibitors, such as, for example, erectile dysfunction or colics of the kidneys and the ureters in connection with kidney stones. In addition, the compounds according to the invention can be employed for the treatment of diabetes insipidus and disorders in connection with disturbances of brain metabolism, such as, for example, cerebral senility, senile dementia (Alzheimer's dementia), multiinfarct dementia or alternatively disorders of the CNS, such as, for example, depressions or arteriosclerotic dementia.

A further subject of the invention is a process for the treatment of mammals, including man, which are suffering from one of the abovementioned illnesses. The process comprises administering to the sick mammal a therapeutically efficacious and pharmacologically tolerable amount of one or more of the compounds according to the invention.

The invention further relates to the compounds according to the invention for use in the treatment and/or prophylaxis of illnesses, in particular the illnesses mentioned.

The invention likewise relates to the use of the compounds according to the invention for the production of medicaments which are employed for the treatment and/or prophylaxis of the illnesses mentioned.

Medicaments for the treatment and/or prophylaxis of the illnesses mentioned, which contain one or more of the compounds according to the invention, are furthermore a subject of the invention.

A further subject of the invention is a commercial product, consisting of a customary secondary pack, a primary pack containing the medicament (for example an ampoule or a blister pack) and, if desired, a pack insert, the medicament exhibiting antagonistic action against cyclic nucleotide phosphodiesterases of type 4 (PDE4) and leading to the attenuation of the symptoms of illnesses which are connected with cyclic nucleotide phosphodiesterases of type 4, and the suitability of the medicament for the prophylaxis or treatment of illnesses which are connected with cyclic nucleotide phosphodiesterases of the type 4 being indicated on the secondary pack or on the pack insert of the commercial product, and the medicament containing one or more compounds of the formula I according to the invention. The secondary pack, the primary pack containing the medicament and the pack insert otherwise comply with what would be regarded as standard to the person skilled in the art for medicaments of this type.

The medicaments are prepared by processes which are known per se and familiar to the person skilled in the art. As medicaments, the compounds according to the invention (=active compounds) are either employed as such, or preferably in combination with suitable pharmaceutical excipients, e.g. in the form of tablets, coated tablets, capsules, suppositories, patches, emulsions, suspensions, gels or solutions, the active compound content advantageously being between 0.1 and 95%.

The person skilled in the art is familiar on the basis of his/her expert knowledge with the excipients which are suitable for the desired pharmaceutical formulations. In addition to solvents, gel-forming agents, ointment bases and other active compound vehicles, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this, these are either administered directly as a powder (preferably in micronized form) or by nebulization of solutions or suspensions which contain them. With respect to the preparations and administration forms, reference is made, for example, to the details in European Patent 163 965.

For the treatment of dermatoses, the compounds according to the invention are in particular used in the form of those medicaments which are suitable for topical application. For the production of the medicaments, the compounds according to the invention (=active compounds) are preferably mixed with suitable pharmaceutical excipients and further processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by methods known per se. Dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.1 and 3 mg per day. The customary dose in the case of systemic therapy (p.o. or i.v.) is between 0.03 and 3 mg per kilogram per day.

BIOLOGICAL INVESTIGATIONS

In the investigation of PDE4 inhibition at the cellular level, the activation of inflammatory cells has particular importance. As an example, the FMLP (N-formyl-methionyl-leucyl-phenylalanine)-induced superoxide production of neutrophilic granulocytes may be mentioned, which can be measured as luminol-potentiated chemoluminescence [McPhail L C, Strum S L, Leone P A and Sozzani S, The neutrophil respiratory burst mechanism. In "Immunology Series" 1992, 57, 47–76; ed. Coffey R G (Marcel Decker, Inc. New York-Basle-Hong Kong)].

Substances which inhibit chemoluminescence and cytokine secretion and the secretion of inflammatory mediators on inflammatory cells, in particular neutrophilic and eosinophilic granulocytes, T lymphocytes, monocytes and macrophages, are those which inhibit PDE4. This isoenzyme of the phosphodiesterase families is particularly represented in granulocytes. Its inhibition leads to an increase in the intracellular cyclic AMP concentration and thus to the inhibition of cell activation. PDE4 inhibition by the substances according to the invention is thus a central indicator of the suppression of inflammatory processes (Giembycz MA, Could isoenzyme-selective phosphodiesterase inhibitors render bronchodilatory therapy redundant in the treatment of bronchial asthma?. Biochem Pharmacol 1992, 43, 2041–2051; Torphy T J et al., Phosphodiesterase inhibitors: new opportunities for treatment of asthma. Thorax 1991, 46, 512–523; Schudt C et al., Zardaverine: a cyclic AMP PDE ¾ inhibitor. In "New Drugs for Asthma Therapy", 379–402, Birkhäuser Verlag Basle 1991; Schudt C et al., Influence of selective phosphodiesterase inhibitors on human neutrophil functions and levels of cAMP and Ca; Naunyn-Schmiedebergs Arch Pharmacol 1991, 344, 682–690; Tenor H and Schudt C, Analysis of PDE isoenzyme profiles in cells and tissues by pharmacological methods. In "Phosphodiesterase Inhibitors", 21–40, "The Handbook of Immunopharmacology", Academic Press, 1996; Hatzelmann A et al., Enzymatic and functional aspects of dual-selective PDE¾-inhibitors. In "Phosphodiesterase Inhibitors", 147–160. "The Handbook of Immunopharmacology", Academic Press, 1996).

Inhibition of PDE4 activity

Methodology

The activity test was carried out according to the method of Bauer and Schwabe, which was adapted to microtiter plates (Naunyn-Schmiedeberg's Arch. Pharmacol. 1980, 311, 193–198). The PDE reaction takes place in the first step here. In a second step, the resulting 5'-nucleotide is cleaved by a 5'- nucloetidase of the snake venom of Crotalus atrox to the uncharged nucleoside. In the third step, the nucleoside is separated from the remaining charged substrate on ion-exchange columns. The columns are eluted directly into minivials, into which 2 ml of scintillator fluid are additionally added, for counting using 2 ml of 30 mM ammonium formate (pH 6.0).

The inhibitory values determined for the compounds according to the invention [inhibitory concentration as -log $IC_{50}$ (mol/l)] follow from the following Table A, in which the numbers of the compounds correspond to the numbers of the examples.

TABLE A

Inhibition of the PDE4 activity

| Compound | -log $IC_{50}$ |
|---|---|
| 1 | 8.24 |
| 2 | 8.25 |
| 3 | 8.70 |
| 4 | 8.11 |
| 5 | 8.58 |
| 6 | 8.02 |
| 7 | 8.54 |

What is claimed is:
1. A compound of formula I

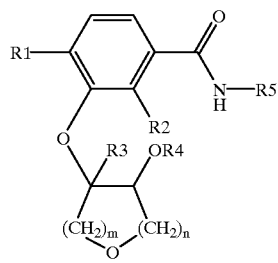

(I)

in which
R1 is 1–6C-alkoxy, 3–7C-cycloalkoxy, 3–7C-cycloalkylmethoxy, benzyloxy or 1–4C-alkoxy which is completely or predominantly substituted by fluorine, R2 is hydrogen and
R3 is hydrogen
or
R2 and R3 are together a methylene group,
R4 is hydrogen, 1–8C-alkyl, 1–6C-alkoxy-1–4C-alkyl, 1–6C-alkylthio-1–4-alkyl, 1–6C-alkylsulfinyl-1–4C-alkyl, 1–6C-alkylsulfonyl-1–4C-alkyl, 1–8C-alkylcarbonyl, 3–7C-cycloalkyl, 3–7C-cycloalkymethyl, phenyl-1–4C-alkyl or 1–4C-alkyl which is completely or predominantly substituted by fluorine,
R5 is phenyl, pyridyl, phenyl substituted by R51, R52 and R53 or pyridyl substituted by R54, R55, R56 and R57, where
R51 is hydroxyl, halogen, cyano, carboxyl, trifluoromethyl, 1–4C-alkyl, 1–4C-alkoxy, 1–4C-alkoxycarbonyl, 1–4C-alkylcarbonyl, 1–4C-alkylcarbonyloxy, amino, mono- or di-1–4C-alkylamino or 1–4C-alkylcarbonylamino,
R52 is hydrogen, hydroxyl, halogen, amino, trifluoromethyl, 1–4C-alkyl or 1–4C-alkoxy,
R53 is hydrogen, halogen, 1–4C-alkyl or 1–4C-alkoxy,
R54 hydroxyl, halogen, cyano, carboxyl, 1–4C-alkyl, 1–4C-alkoxy, 1–4C-alkoxycarbonyl or amino,
R55 is hydrogen, halogen, amino or 1–4C-alkyl,
R56 is hydrogen or halogen and
R57 is hydrogen or halogen,
n is 1 or 2,
m is 1 or 2,
where the sum of m and n may only assume the values 2 or 3, a salt of these compounds and the N-oxide of the pyridines or a salt thereof.

2. A compound of formula I according to claim 1 in which
R1 is 1–4C-alkoxy, 3–5C-cycloalkoxy, 3–5C-cycloalkylmethoxy or 1–4C-alkoxy which is completely or predominantly substituted by fluorine,
R2 is hydrogen and
R3 is hydrogen,
or
R2 and R3 together are a methylene group,
R4 is hydrogen, 1–6C-alkyl, 1–4C-alkoxy-1–4C-alkyl, 1–4C-alkylthio-1–4C-alkyl, 1–6C-alkylcarbonyl, 3–7C-cycloalkyl, 3–7C-cycloalkylmethyl, phenyl-1–4C-alkyl or 1–4C-alkyl which is completely or predominantly substituted by fluorine,
R5 is phenyl, pyridyl, phenyl substituted by R51, R52 and R53 or pyridyl substituted by R54, R55, R56 and R57, where
R51 is halogen, cyano, carboxyl, 1–4C-alkyl, 1–4C-alkoxy or 1–4C-alkoxycarbonyl,
R52 is hydrogen, halogen, 1–4C-alkyl or 1–4C-alkoxy,
R53 is hydrogen, halogen, 1–4C-alkyl or 1–4C-alkoxy,
R54 is halogen or 1–4C-alkyl,
R55 is hydrogen or halogen,
R56 is hydrogen or halogen and
R57 is hydrogen or halogen,
n is 1 or 2,
m is 1 or 2,
where the sum of m and n may only assume the values 2 or 3, a salt of these compounds and the N-oxide of the pyridines or a salt thereof.

3. A compound of formula I according to claim 1 in which
R1 is methoxy or difluoromethoxy,
R2 is hydrogen and R3 is hydrogen or R2 and R3 together are a methylene group, R4 is hydrogen, 1–6C-alkyl, 1–4C-alkoxy-1–4C-alkyl, 1–4C-alkylthio-1–4C-alkyl, 1–4C-alkylcarbonyl, phenethyl or benzyl, R5 is 2-bromophenyl, 2-chlorophenyl, 2,6-dichloro-4-ethoxycarbonylphenyl, 2,6-dimethoxyphenyl, 4-cyano-2-fluorophenyl, 2,4,6-trifluorophenyl, 2-chloro-6-methylphenyl, 2,6-dimethylphenyl, 2-chloro-6-fluorophenyl, 2,6-difluorophenyl, 2,6-dichlorophenyl, 3,5-dichloropyrid-4-yl, 3-methylpyrid-2-yl, 2-chloropyrid-3-yl, 3-chloropyrid-4-yl, 3,5-dibromopyrid-2-yl, 3,5-difluoropyrid-4-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl, n is 1, m is 1 and a salt the thereof and the N-oxide of the pyridines or a salt thereof.

4. A compound of formula I according to claim 1 in which

R1 is methoxy or difluoromethoxy,

R2 is hydrogen and

R3 is hydrogen, or

R2 and R3 together are a methylene group,

R4 is hydrogen, 1–4C-alkyl, 1–2C-alkoxy-1–2C-alkyl, 1–2C-alkylthio-1–2C-alkyl, 1–4C-alkylcarbonyl or benzyl, R5 is 3,5-dichloropyrid-4-yl, 2-chloropyrid-3-yl, 3-chloropyrid-4-yl, 3,5-dibromopyrid-2-yl, 3,5-difluoropyrid-4-yl, 2,3,5,6-tetrafluoropyrid-4-yl, 3-chloro-2,5,6-trifluoropyrid-4-yl, 3,5-dichloro-2,6-difluoropyrid-4-yl or 2,6-dichloropyrid-3-yl, n is 1, m is 1 and a salt of thereof an and the N-oxide of the pyridines salt thereof.

5. A compound of formula I according to claim 1 in which

R1 is methoxy,

R2 is hydrogen and

R3 is hydrogen, or

R2 and R3 together are a methylene group,

R4 is hydrogen, methyl, ethyl, methylthiomethyl or benzyl,

R5 is 3,5-dichloropyrid-4-yl, n is 1, m is 1 and a salt thereof.

6. A compound according to claim 1, in which R2 and R3 are hydrogen.

7. A compound according to claim 1, in which R2 and R3 together are a methylene group.

8. A medicament comprising one or more compounds as claimed in claim 1 together with a usual pharmaceutical excipient and/or vehicle.

9. A method of treating a condition amenable to treatment with a selective cyclic nucleotide phosphodiesterase (PDE) inhibitor which comprises administering an effective amount of a compound as claimed in claim 1, a pharmacologically-acceptable salt thereof, an N-oxide of a pyridine thereof or a pharmacologically acceptable salt of the latter to a subject afflicted with such condition.

10. A method of compounding a medicament composition for treating an airway disorder by combining a selective cyclic nucleotide phosphodiesterase (PDE) inhibitor with a pharmaceutical incipient and/or vehicle, wherein the PDE inhibitor is a compound according to claim 1, a pharmacologically acceptable salt thereof, an N-oxide of a pyridine thereof or a pharmacologically acceptable salt of the latter.

* * * * *